United States Patent [19]
Essex et al.

[11] Patent Number: 5,736,391
[45] Date of Patent: Apr. 7, 1998

[54] HIV GP41 MUTANTS

[75] Inventors: Myron E. Essex, Sharon; Xiaofang Yu, Jamaica Plain; Tun-Hou Lee, Newton, all of Mass.

[73] Assignee: President and Fellows of Harvard College, Cambridge, Mass.

[21] Appl. No.: 467,933

[22] Filed: Jun. 6, 1995

Related U.S. Application Data

[63] Continuation of Ser. No. 979,975, Nov. 23, 1992, abandoned.

[51] Int. Cl.$^6$ .................. C12N 15/49; C12N 15/79; C07H 21/04; A61K 48/00
[52] U.S. Cl. .................. 435/320.1; 514/44; 536/23.5; 536/23.72; 930/221
[58] Field of Search .................. 514/44; 424/93.1, 424/93.2, 93.21; 536/23.5, 23.72; 930/221

[56] References Cited

PUBLICATIONS

M.I. Johnston et al. (1993) Science 260:1286–1293.

D. Cournoyer et al. (1993) Annu. Rev. Immunol. 11:297–329.

M.B. Feinberg et al. (1992) AIDS Res. and Human Retrovir. 8(6):1013–1022.

J.A.T. Young et al. (1990) Science 250:1421–1423.

G.L. Buchschacher, Jr. et al (1992) Human Gene Therapy 3:391–397.

X. Yu et al. (Jul. 19–24, 1992) Int. Conf. AIDS 8(1):PTU31, (abstract No. TUA 0526).

J.W. Dubay et al (1989) J. Cell. Biochem. Suppl. 13 Part B: 268, (abstract G213).

J. W. Dubay et al. Truncation of the Human Immunodeficiency Virus Type 1 Transmembrane Glycoprotein Cytoplasmic Domain Blocks Virus Infectivity vol. 66, No. 11, Nov. 1992, pp. 6616–6625.

Gabuzda et al., Effects of Deletions in the Cytoplasmic Domain on Biological Functions of Human Immunodeficiency Virus Type 1 Envelope Glycoproteins, J. Virology 66:3306–3315, 1992.

Natsoulis and Boeke, New Antiviral Strategy Using Capsid–nuclease Fusion Proteins, Nature 352:632–635, 1991.

Pal et al., Myristoylation of gag Proteins of HIV–1 Plays an Important Role in Virus Assembly, AIDS Research and Human Retroviruses 6:721–730, 1990.

Smith et al., Human Immunodeficiency Virus Type 1 Pr55$^{gag}$ and Pr160$^{gag-pol}$ Expressed from a Simian Virus 40 Late Replacement Vector are . . . Assembled into Viruslike Particles, J. Virology 64:2743–2750, 1990.

Trono et al., HIV–1 Gag Mutants can Dominantly Interfere with the Replication of the Wild–Type Virus, Cell 59:113–120, 1989.

Arthos et al., Identification of the Residues in Human CD4 Critical for the Binding of HIV, Cell 57:469–481, 1989.

Dubay et al., Truncation of the Human Immunodeficiency Virus Type 1 Transmembrane Glycoprotein Cytoplasmic Domain Blocks Virus Infectivity, J. Virology 66:6616–6625, 1992.

Earl et al., Biological and Immunological Properties of Human Immunodeficiency Virus Type 1 Envelope Glycoprotein: Analysis of Proteins with . . . Recombinant Vaccinia Viruses J. Virology 65:31–41, 1991.

Freed et al., Characterization of the Fusion Domain of the Human Immunodeficiency Virus Type 1 Envelope Glycoprotein gp41, Proc. Natl. Acad. Sci. USA 87:4650–4654, 1990.

(List continued on next page.)

*Primary Examiner*—John L. LeGuyader
*Assistant Examiner*—Johnny F. Railey, II
*Attorney, Agent, or Firm*—Fish & Richardson P.C.

[57] ABSTRACT

Nucleic acid constructs encoding mutated human immunodeficiency virus gp41 polypeptides are described. The mutated polypeptides are effective to disrupt viral replication of HIV or disrupt the assembly of viral Env proteins in an HIV infected cell.

5 Claims, 16 Drawing Sheets

OTHER PUBLICATIONS

Freed et al., A Mutation in the Human Immunodeficiency Virus Type 1 Transmembrane Glycoprotein gp41 Dominantly Interferes with Fusion and Infectivity, Proc. Natl. Acad. Sci. USA 1992.

Friedmann, Progress Toward Human Gene Therapy, Science 244:1275–1281, 1989.

Guy et al., A Specific Inhibitor of Cysteine Proteases Impairs a Vif-Dependent Modification of Human Immunodeficiency Virus Type 1 Env Protein, J. Virology 65:1325–1331, 1991.

Haffar et al., The Carboxy Terminus of Human Immunodeficiency Virus Type 1 gp160 Limits its Proteolytic Processing and Transport in Transfected Cell Lines.

Ivey-Hoyle et al., The N-terminal 31 Amino Acids of Human Immunodeficiency Virus Type 1 Envelope Protein gp120 Contain a Potential gp41 Contact Site. J. Virology 65:2682–2685, 1991.

Kowalski et al, Attenuation of Human Immunodeficiency Virus Type 1 Cytopathic Effect by a Mutation Affecting the Transmembrance Envelope Glycoprotein, J. Virology, 65:281–291, 1991.

Lasky et al., Delineation of a Region of the Human Immunodeficiency Virus Type 1 gp120 Glycoprotein Critical for Interaction with the CD4 Receptor, Cell 50:975–985, 1987.

Lee et al., Role of the Carboxy-Terminal Portion of the HIV-1 Transmembrane Protein in Viral Transmission and Cytopathogencity, Aids Research and Human Retroviruses 5:441–449, 1989.

Shimizu et al., Analysis of a Human Immunodeficiency Virus Type 1 Isolate Carrying a Truncated Transmembrance Glycoprotein, Virology 189:534–546, 1992.

```
                              H       E AS               FF
                              N       C PC               OI
MB                            F       R YR               KN
AS                            1       2 1                1 1
EM                                                          \
11                                                           \
   TTGGAATGCTAGTTGGAGTAATAAATCTCTGGAACAGATTTGGAATCACACGACCTGGATGGAGTGGGAC
   ----+----+----+----+----+----+----+----+----+----+----+----+----+----  8120
   AACCTTACGATCAACCTCATTATTTAGAGACCTTGTCTAAACCTTAGTGTGCTGGACCTACCTCACCCTG
    g m l v g v l n l w n r f g l t r p g w s g t
    l e c . l e . l s g t d l e s h d l d g v g q
    w n a s w s n k s l e q l w n h t t w m e w d

M       M H                M
                              S       S N                B
HAM                           E       E F                O
ILS                           1       1 1                2
NUE
311                                                         \
   AGAGAAATTAACAATTACACAAGCTTAATACACTCCTTAATTGAAGAATCGCAAACCAGCAAGAAAAGA
   ----+----+----+----+----+----+----+----+----+----+----+----+----+----  8190
   TCTCTTTAATTGTTAATGTGTTCGAATTATGTGAGGAATTAACTTCTTAGCGTTTTGGTCGTTCTTTCT
    e k l t i t q a . y t p l k n r k t s k k r
    r n . q l h k l n t l n . r l a k p a r k e
    r e l n n y t s l l h s l l e e s q n q q e k n
```

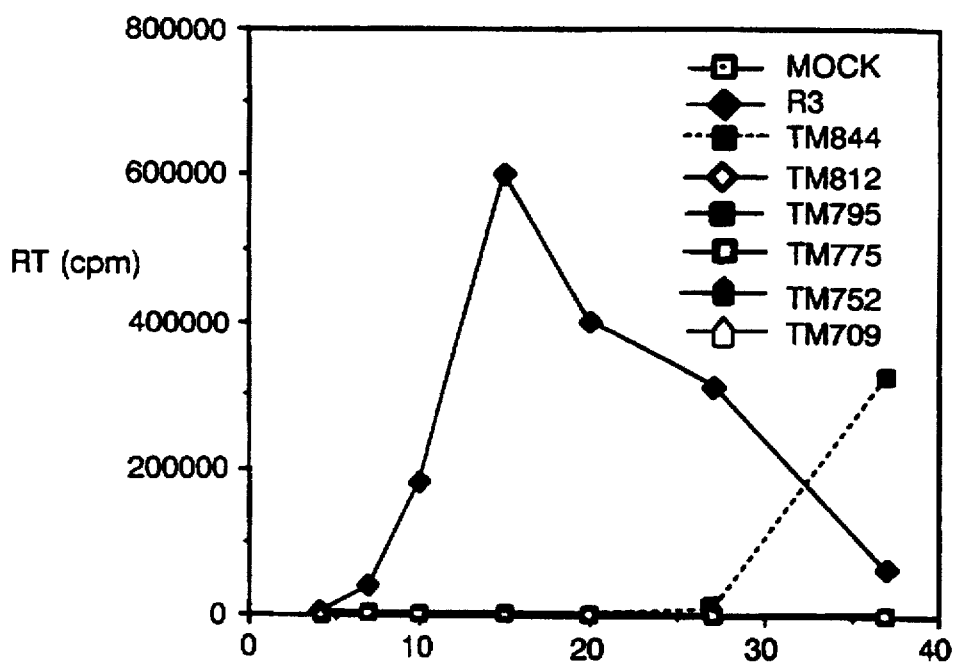
FIG. 3A  DAYS AFTER INJECTION (SUP-T1)
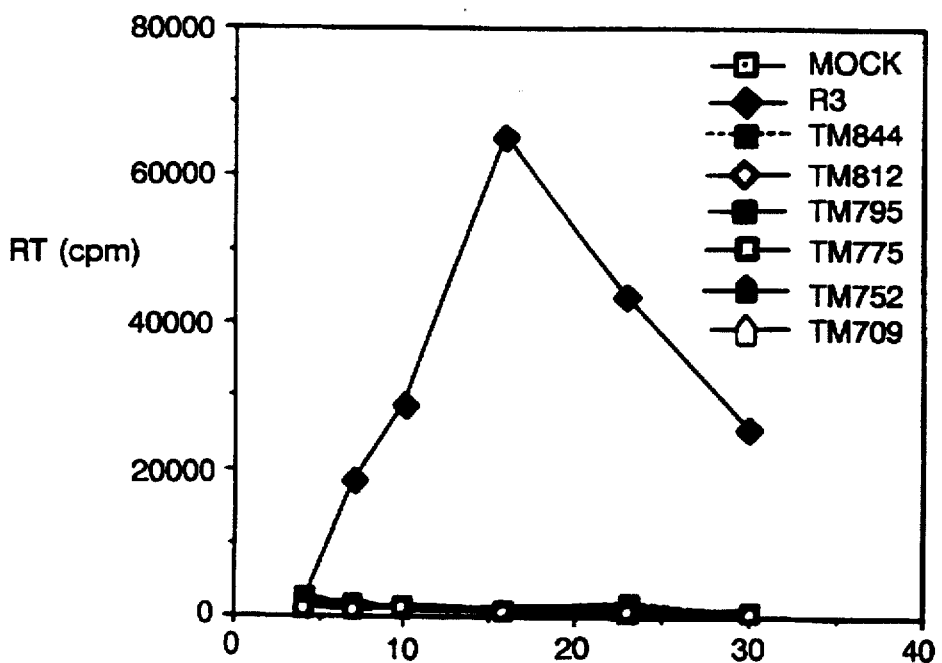
FIG. 3B  DAYS AFTER INJECTION (H-9)

HIV GP41 MUTANTS

This is a continuation of application Ser. No. 07/979,975, filed Nov. 23, 1992, now abandoned.

STATEMENT AS TO FEDERALLY SPONSORED RESEARCH

This invention was funded at least in part by the United States government and the government has certain rights in the invention.

BACKGROUND OF THE INVENTION

This invention relates to the treatment of infection with the human immunodeficiency virus (HIV), by which we mean to include all of the various viral types and strains denominated by that term, such as HTLV-III, LAV, ARV, HIV-1, HIV-2, and LAV-2.

HIV is an etiological agent of Acquired Immune Deficiency Syndrome (AIDS). An example of HIV (now denominated HIV-1) is generally described in several articles: Barre-Sinoussi et al., *Science* 220:868, 1983; Gallo et al., *Science* 224:500, 1984; Popovic et al., *Science* 224:497, 1984; and Levy et al., *Science* 225:840, 1984, each of which is hereby incorporated by reference. Various isolates of HIV-1 have been obtained from North America, Western Europe and Central Africa. These isolates differ somewhat in their nucleotide sequence, but the proteins they encode are generally antigenically cross-reactive.

A second virus related to HIV-1 has been isolated and termed HIV-2. This virus is reported by Guyader et al., *Nature* 326:662, 1987; Brun-Vezinet et al., *The Lancet* 1:128, 1987; and Clavel et al., *Science* 233:343, 1986, each of which is hereby incorporated by reference. The genetic organization of HIV-2 is similar to that of HIV-1.

A group of viruses isolated from monkeys, termed simian immunodeficiency virus (SIV or STLV-III), is related to HIV-1 and HIV-2, particularly the latter. See Daniel et al., *Science* 228:1201–1204 (1985); Kanki et al., *Science* 230:951–954 (1985); Chakrabarti et al., *Nature* 328:543–547 (1987); and Ohta et al., *Int'l. J. Cancer* 41:115–222 (1988), each of which is hereby incorporated by reference. Members of this viral group exhibit minor variations in their genomic sequences, and have some differences in their restriction enzyme maps.

As with other lentiviruses, HIV encodes an envelope precursor protein that is processed into a transmembrane (TM) protein and an extracellular protein. The TM protein extends further downstream from the transmembrane domain (Gallaher, W. R. et al., *AIDS Res. Hum. Retroviruses* 5:431–440 (1989); Hunter and Swanstrom, Current Topics in Microbiology and Immunology 157:187–253 (1990)), resulting in a long cytoplasmic domain of more than 100 amino acids. For example, the cytoplasmic domain of HIV-1, HIV-2, and SIV TM proteins consists of approximately 150 amino acids (Gallaher, W. R. et al., *AIDS Res. Hum. Retroviruses* 5:431–440 (1989); Hunter and Swanstrom, Current Topics in Microbiology and Immunology 157:187–253 (1990)). For SIV and HIV-2, it is reported that a large portion of the cytoplasmic domain of the TM protein is dispensable for viral replication in certain established human cell lines (Chakrabarti et al., *Nature* 328:543–547 (1987); Fukasawa et al., *Nature* 333:457–461 (1988); Guyader et al., *Nature* 236:662–669 (1987); Hirsch et al., *Cell* 49:307–319 (1987)). Some natural SIV and HIV-2 isolates which have truncated TM proteins propagate better than viruses with full length TM proteins in certain established human cell lines (Chakrabarti et al., *J. Virol* 63:4395–4403, (1989); Hirsch et al., *Nature* 341:573–574 (1989); Kodama et al., *J. Virol.* 63:4709–4714 (1989)). It is also reported that the truncated TM protein has increased fusogenic ability. ((Earl et al., *J. Virol.* 65:31–41 (1991); Kowalski et al., *Science* 237:1351–1355 (1987); Mulligan, M. J. et al., *J. Virol.* 66:3971–3975 (1992); Mulligan et al., *J. Virol.* 66:3971–3975 (1992)).

In contrast to SIV and HIV-2, infectious HIV-1 clones that have been sequenced to date generally contain a full length TM protein (gp41). Computer analysis indicates that the cytoplasmic domain of gp41 contains two amphipathic α helical structures (Venable et al., *AIDS Res. Hum. Retroviruses* 5:7–22 (1989)) which can form a secondary association with the membrane bilayer (Haffar et al., *Virology* 180:439–441 (1991)). It has been reported that deleting large truncations deleting both of the α helices in the cytoplasmic domain of gp41 did not significantly affect viral Env protein biosynthesis, processing, transport or surface expression (Earl et al., *J. Virol* 65:31–41, (1991)). Syncytium formation (Earl et al., *J. Virol.* 65:31–41 (1991); Kowalski et al., *Science* 237:1351–1355 (1987)) and oligomerization (Earl et al., *Proc. Natl. Acad. Sci. USA* 87:648–652 (1990)) of the mutant Env protein reportedly were also not impaired.

HIV has already entered large segments of the world population, and substantial effort has been directed toward developing treatments for individuals infected with it. In addition to the investigation of synthetic pharmaceuticals, effort has been directed toward utilizing variants of HIV-1 and HIV-2 to design AIDS therapeutics (Trono et al., *Cell,* 59:113–120, (1989).

Intracellular "immunization" using gag p24 core gene mutants or capsid targeted Gag-nuclease fusion molecules have been described as potential anti-retroviral strategies (Trono et al., *Cell* 59:113–120 (1989); Natsoulis et al., *Nature* 352:632–635 (1991)).

SUMMARY OF THE INVENTION

The invention features a method of treating a patient infected with human immunodeficiency virus (HIV) by administering a mutant of the gp41 polypeptide in an amount effective to reduce infective HIV levels in the patient. The gp41 polypeptides may be delivered by various vehicles as described below.

The mutated gp41 polypeptide may be administered as the polypeptide itself or as an expressible genetic construction including nucleic acid encoding the mutated gp41. The nucleic acid used may be nucleic acid capable of transforming cells of the patient and may be administered as a part of a viral vector. The nucleic acid used may further include a sequence encoding a CD4-binding polypeptide, a sequence encoding a gp120-binding polypeptide, or fragments thereof which enable entry of the therapeutic peptide into the target cell. Such therapeutics are administered in a pharmaceutically acceptable carrier.

Also included as a part of the invention is a method for transforming the cells outside of the patient's body and returning the transformed cells to the patient. Preferably the cells are removed from the patient, before they are transformed with the nucleic acid, and returned to the patient's body.

Alternatively, the nucleic acid may be administered directly to the patient and/or may be delivered in a viral vector which is a derivative of the human immunodeficiency virus-type I.

The invention further includes methods of treating an HIV infected patient by the administration of a mutant gp41 polypeptide which contains a deletion of at least one amino acid in at least one of the following regions of wild type gp41:

amino acids 844 to 856;
amino acids 814 to 856;
amino acids 796 to 856;
amino acids 776 to 856;
amino acids 753 to 856; or
amino acids 710 to 856, effective to disrupt the viral replication of HIV or assembly of Env proteins in an infected cell. Preferably, such deletions will include between 40 and 60 percent of the stated deletions, and, more preferably, between 60 and 80% of the stated deletions and most preferably, between 80 and 100% of the stated deletions.

Also included as a part of the invention are therapeutic compositions adapted for administration to a patient infected with human immunodeficiency virus-type I (HIV). These compositions include a mutated gp41 polypeptide in a pharmaceutically acceptable carrier, or a nucleic acid encoding a mutated gp41 polypeptide in an expressible genetic construction for transforming cells of a human patient.

The therapeutic composition may include the nucleic acid as part of a viral vector capable of transforming cells of the patient. The nucleic acid may further include a sequence capable of encoding a CD4-binding polypeptide, a sequence encoding a gp120-binding polypeptide, or fragments thereof.

By mutated gp41 is meant a gp41 having a deletion, insertion, substitution, or other modification rendering gp41 effective as an inhibitor of HIV viral assembly and infectivity as demonstrated by one of the assays described below.

The mutated gp41 polypeptides included in the invention may be the equivalent mutated gp41 proteins from other strains of HIV. Where we have designated the mutation site by number, one skilled in the art may determine the equivalent mutations in HIV and proteins whose sequence differs from FIG. 1; based upon amino acid and nucleic acid homology.

Those mutations which disrupt the incorporation of Env proteins and/or viral replication and are useful therapeutics for patients infected with HIV may be determined using the techniques described in the methods, below. Particularly useful are the transfection, infection, and RT assay and radioimmunoprecipitation, immunoblot, and plus chase analysis procedures. Specifically, useful mutant gp41 polypeptides and nucleic acids encoding polypeptides will be those which disrupt Env protein incorporation and which result in normal levels of the gag and pol proteins, but confer decreased levels of gp120 and gp41 proteins in the virion. Useful mutant gp41 polypeptides which disrupt viral replication are those which decrease viral replication relative to wild-type virus, preferably decreasing replication by 10% and most preferably decreasing replication by 20% or more in a co-transfection assay.

Other features and advantages of the invention will be apparent from the following description of the preferred embodiments of the invention and from the claims.

DESCRIPTION OF THE PREFERRED EMBODIMENTS

The drawings will first be briefly described.

Drawings FIG. 1 diagrams the sequence of DNA encoding the gp41 polypeptide and the primary amino acid sequence of the gp41 polypeptide.

Figure 2:
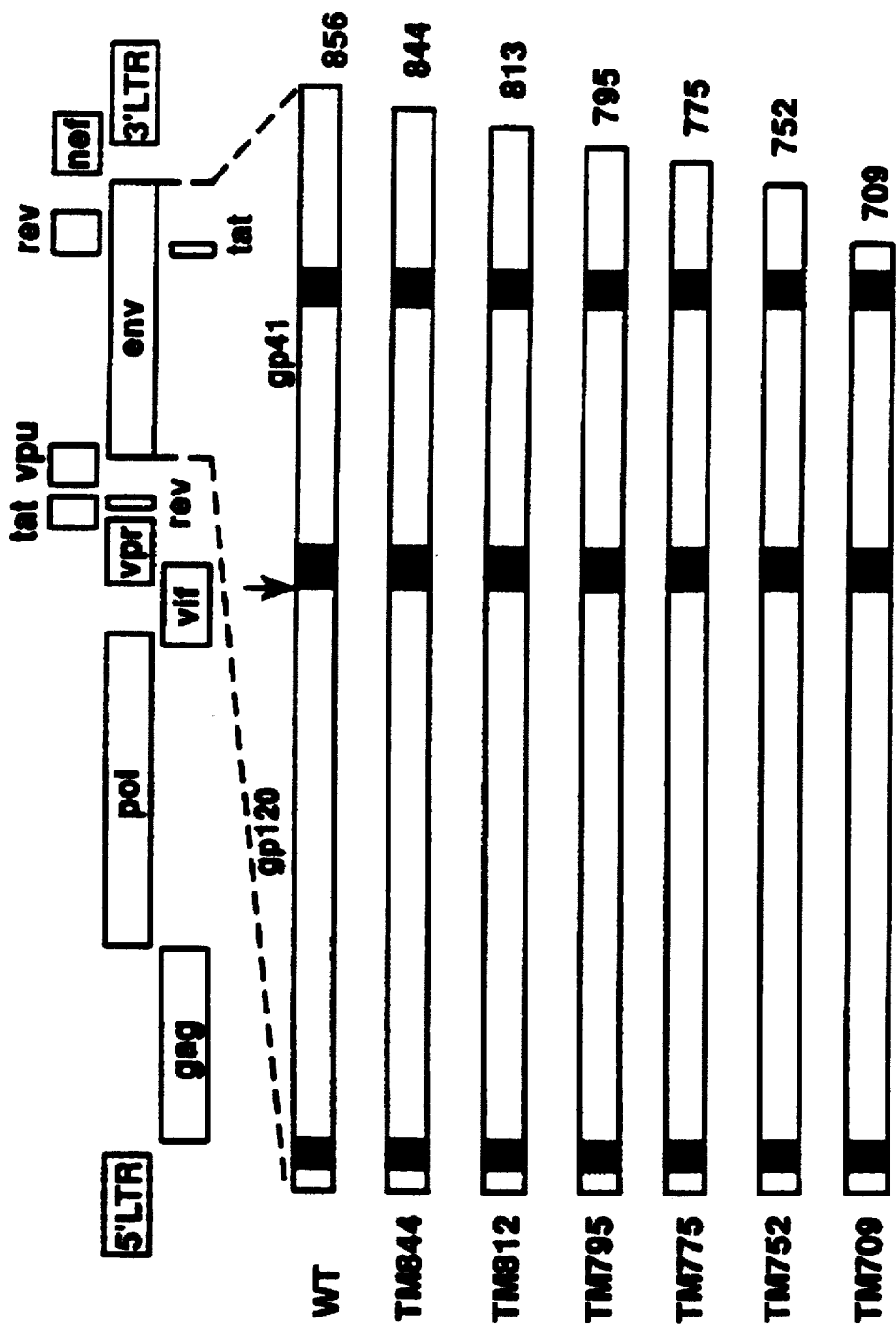

FIG. 2 is a diagram representing the construction of gp41 mutants. The HIV-1 Env precursor protein contains 856 amino acids in HXB2R3. The darkened areas represent hydrophilic regions. The arrow indicates the cleavage site between gp120 and gp41. The numbers at the end of each diagram indicate the last amino acid that can be synthesized in gp160 by each construct, except for TM812 which terminates after amino acid 813.

Figure 3C:
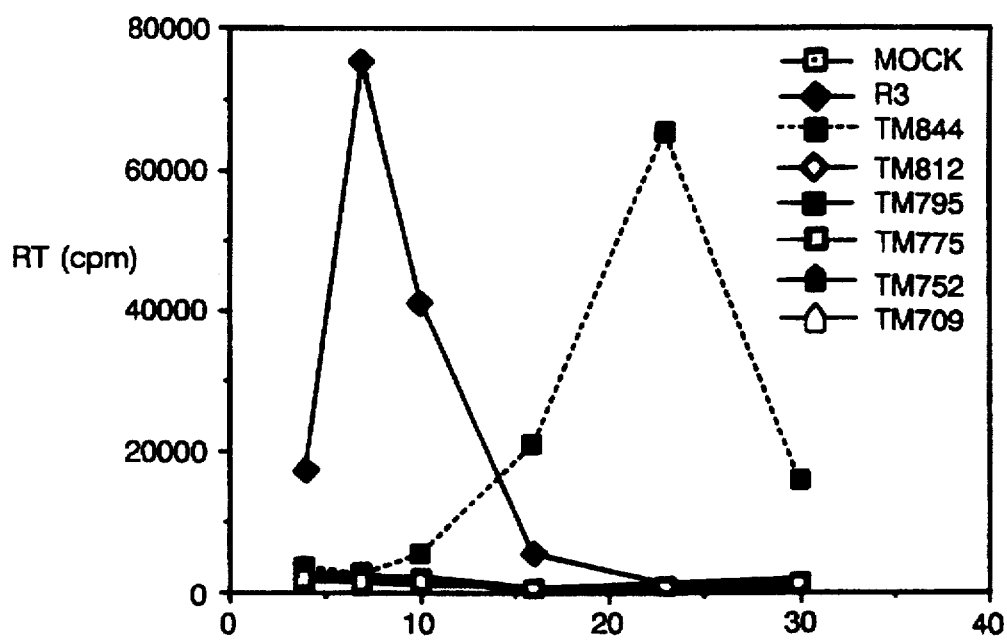
Figure 3D:
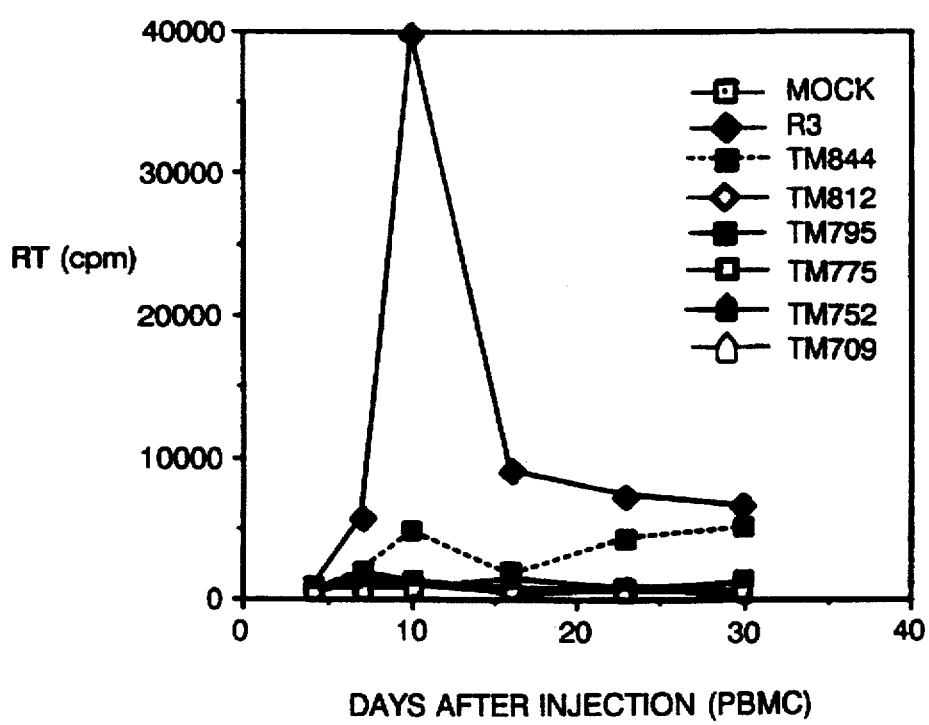

FIG. 3 is a series of graphs representing a virus infectivity assay. Cell-free wild type and mutant viruses were prepared from the supernatants of transfected COS-7 cells and tested on SupT1, MT-2, H9, and fresh PBMC. Reverse Transcriptase (RT) values represent samples form 0.1 ml culture supernatants, measured in counts per minute (cpm).

FIG. 4 (parts A and B) depicts analysis of viral proteins by immunoblot. (A) Purified and analyzed. (B) Cell lysates (cell) and sucrose gradient purified virions (virus) blotted with another HIV-1 positive human sera.

FIG. 5 (parts A and B) (A) depicts analysis of viral proteins by radioimmunoprecipitation. Cell lysates (cell) and supernatants (sup) from [$^{35}$S] cysteine metabolically labeled transfected COS-7 cells were reacted with the HIV-1-positive sera. (B) depicts surface expression of HIV-1 Env proteins detected by indirect immunofluorescence using mouse monoclonal antibody against gp120; a and b are mock-transfected cells; c and d are wt-transfected cells; e and f are TM752-transfected cells; g and h are TM709-transfected cells. The corresponding Nomarsky pictures (a, c, e and g) are adjacent to the florescence pictures (b, d, f and h).

Figure 6:
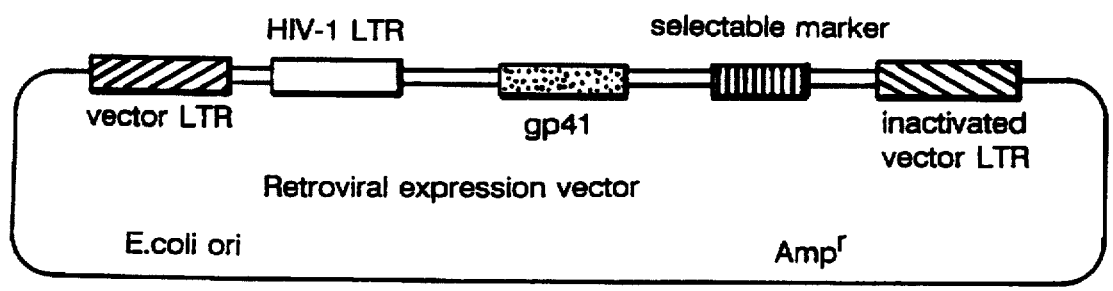

FIG. 6 depicts a viral construct with the nucleic acid encoding gp41 in an expressible position.

I. gp41 Polypeptides for Use as Anti-HIV Therapeutics

Without wishing to bind ourselves to a specific mechanism of action, it appears that mutant gp41 polypeptides are useful as anti-HIV therapeutics because they interfere with the incorporation of viral env proteins into infectious viral particles in an HIV infected cell. As the examples below demonstrate, mutations which delete or otherwise disrupt the carboxy-terminal domain of gp41 have this property and are anti-HIV therapeutics. While env protein synthesis is not disrupted in such mutants, the incorporation of the viral Env proteins into infectious particles is significantly impaired. This failure to properly incorporate the Env proteins results in noninfectious particles. This dominant quality of the mutants with respect to wild-type virus is also referred to as a "dominant-negative" property.

Moreover, mutations outside the carboxy terminal domain which disrupt the interaction between gp41 and the Env proteins, particularly mutations in the transmembrane domain, may yield effective therapeutics.

Some gp41 polypeptides useful for this purpose include deletions which remove greater than twelve but no more than 147 amino acids from the carboxy terminus. Most useful for disruption of viral assembly are those mutations which remove between 104 and 147 amino acids of the carboxy terminal cytoplasmic domain.

Those skilled in the art will appreciate that other gp41 mutations (including deletions, substitutions or additions to naturally occurring (wild type) gp41 sequences) can be used according to the invention. Techniques for generating a universe of candidate mutants are well known to those in the art. A variety of useful techniques are described in *Current Protocols in Molecular Biology*, (eds. Ausebel et al., 1989, Green Publishing Associates, John Wiley & Sons, N.Y., pp. 8.1–8.4). The pool of candidate mutants can then be screened from their ability to disrupt incorporation by various techniques including the techniques described in Examples 2, 3, and 4 and using the dominant negative assay provided below.

Also useful as anti-HIV therapeutics are those gp41 mutations which disrupt the viral replication of pathogenic HIV in an infected cell. Disruption of viral replication may be the result of improper viral assembly or total failure to assemble. Whatever the mechanism, the ability to prevent replication is a useful characteristic of gp41 mutants according to the invention. Mutants having this characteristic can be identified by mutagenesis (described above) followed by screening according to Examples 2, 3, 4 and the dominant negative mutant assay provided, below. Mutations useful for therapy by this mechanism include those mutations which disrupt the most carboxy terminal portion of the cytoplasmic domain. For example, a mutation in gp41 which removes the last 12 amino acids of the carboxy terminus has been demonstrated to be useful for this purpose.

Additional polypeptides useful as gp41 derived anti-HIV therapeutics are described under Other Embodiments.

II. Therapeutic Administration of gp41 Polypeptide

As described in greater detail in the examples below, gp41 mutants according to the invention are effective HIV therapeutics because they may function in a so-called "trans-dominant" fashion. Specifically, it appears that the gp41 mutants become physically associated with an otherwise pathogenic virion components being manufactured in an HIV-infected cells. As a result, the load of properly assembled infections virions that cell manufactures is reduced in proportion to the mutant gp41 levels in the cell. When mutant gp41 is delivered to the cell in sufficient excess, the incidence of ineffective viral assembly results from attempts to incorporate mutant gp41 becomes far higher than the incidence of incorporation of wild type gp41.

With the availability of the cloned gene Rekosh et al., Proc. Natl. Acad. Sci. USA 85:334 (1988), Chanda et al., Vaccines :207 (1989), and Hammarskjold et al., Journal of Virology 63:1959 (1989), the substantially pure gp41 polypeptide mutants can be produced in quantity using standard techniques (Scopes, R. *Protein Purification: Principles and Practice* 1982 Springer-Verlag, N.Y.). Thus, an aspect of the invention is a pharmaceutical comprising the gp41 polypeptide variants together with an acceptable diluent, carrier or excipient and/or in unit dosage form. Conventional pharmaceutical practice may be employed to provide suitable formulations or compositions to administer the polypeptide to patients infected with HIV.

A substantially pure preparation of a polypeptide is a preparation which is substantially free (e.g., to the extent required for formulating the gp41 variant into a therapeutic composition) of the proteins with which it naturally occurs in a cell.

Fragments or analogs of the gp41 protein variant may also be administered to a patient infected with HIV in the manner described herein. Fragments or analogs which are useful for this purpose include fragments and analogs of those mutants in gp41 which are described in the preceding section and in the Examples and which are useful for the treatment of a patient infected with HIV. Fragments and analogs which will be useful for the therapeutic treatment of patients infected with HIV are determined using the assays provided in the examples, below, among others.

The gp41 polypeptide variants may also be administered to a patient infected with HIV in the form of a fusion protein consisting of the desirable gp41 mutant polypeptide fragment, fused to the gp120 protein, or a fragment thereof which is sufficient to bind the CD4 receptor of T cells. The sequences of both the gp120 and CD4 genes for the sates use may be obtained from Rekosh et al., Proc. Natl. Acad. Sci. USA 85:334 (1988), Chanda et al., Vaccines :207 (1989), and Hammarskjold et al., Journal of Virology 63:1959 (1989). This fusion protein allows delivery of the gp41 polypeptide variant into uninfected T cells, monocytes, macrophages or other cell types infected by HIV and expressing the CD4 receptor.

The gp41 polypeptide may also be administered to a patient infected with HIV in the form of a fusion protein consisting of the gp41 polypeptide variant, or a therapeutically useful fragment or derivative, fused to the CD4 protein, or a fragment thereof, which is sufficient to bind gp120. This fusion protein allows delivery of the gp41 polypeptide into infected T cells expressing gp120 on their surface. The gp41-gp120 fusion polypeptide or the gp41-CD4 fusion polypeptide may be generated using standard techniques of molecular biology to generate fusions encoded from a suitable vector (Sambrook et al., *Molecular Cloning: A Laboratory Manual,* Cold Spring Harbor Laboratory Press, New York (1989)).

Either the gp120 fragment or the CD4 fragment may enable internalization of the gp41 polypeptide variant through endocytosis. The usefulness of such gene fusion constructs may be determined using the methods described below in the examples, among others. The invention includes administering either fusion polypeptide alone in a pharmaceutically acceptable carrier, or administering both fusions together in an acceptable carrier.

Thus, the formulations of this invention can be applied for example by parenteral administration, intravenous, subcutaneus, intramuscular, intracranial, intraorbital, opthalmic, intraventricular, intracapsular, intraspinal, intracisternal, intraperitoneal, intranasal, aerosol, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/glycoside copolymer, or polyoxyethylene-polyoxypropylene copolymers may be used to control the release of present factors. Other potentially useful parenteral delivery systems for the factors include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

II B. Construction of HIV Containing gp41

A particularly preferred embodiment features administering to the patient genetic constructions which encode any of the above-described gp41 polypeptides, and (after transformation of patient cells) can express the gp41 polypeptide variant.

In addition to the HIV example below illustrating a preferred viral vehicle, those skilled in the art will readily appreciate that the invention can use other HIV strains of the many that have been fully characterized e.g., MN, HXB2, LAI, NL43, MFA, BRVA and z321.

Moreover, there are numerous other viral vehicles (i.e., nucleic acid vehicles) which can activate or be activated to enter cells of the host organism and, having done so, to be expressed there.

II C. Therapeutic Administration of gp41 variants in a Viral Vector

Retroviral vectors, or other viral vectors with the appropriate tropisms for cells infected by HIV, may be used as a gene transfer delivery system for the gp41 polypeptide variants. Numerous vectors useful for this purpose are generally known have been described (Miller, Human Gene Therapy 15-14 (1990); Friedman, Science 244:1275–1281 (1989); Eglitis and Anderson, BioTechniques 6:608–614 (1988); Tolstoshev and Anderson, Current Opinion in Biotechnology 1:55–61 (1990); Sharp, The Lancet 337:1277–1278 (1991); Cornetta et al., Nucleic Acid Research and Molecular Biology 36:311–322 (1987); Anderson, Science 226:401–409 (1984); Moen, Blood Cells 17:407–416 (1991); and Miller and Rosman, Biotechniques 7:980–990 (1989)). Retroviral vectors are particularly well developed and have been used in a clinical setting (Rosenberg, et al N. Engl. J. Med 323:370 (1990)).

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors. The Moloney murine leukemia retroviral system of gp41 delivery is particularly useful since it targets delivery of the gp41 protein to the hematopoietic cells which ultimately give rise to the T-cells. The delivery of the gp41 polypeptide can be further restricted to cells which are infected by HIV directly by virtue of utilizing retroviral constructs in which the HIV-LTR is used to drive expression from the gp160 gene. To achieve proper expression from such a construct the 3'LTR of the Moloney murine leukemia vector must be deleted. Vector strategies which include either the entire HXB2R3 construct or the gp160 env gene driven by the HIV-LTR (see FIG. 6).

Fragments or derivatives of the gp41 polypeptide may also be administered by retroviral gene transfer therapy or another suitable viral vector system. Fragments or derivatives are defined as described above. Useful fragments or derivatives of gp41 may be administered by inserting the nucleic acids encoding these fragments or derivatives in place of the complete gp160 gene in a gene therapy vector, as described above. Such constructs may be tested using the methods for testing the effects of gp41 on viral infectivity described above, among others.

Retroviral delivery of gp41 is particularly appropriate in HIV infected individuals who display the common secondary appearance of B-cell tumors as a result of immunodeficiency. These individuals may undergo bone marrow removal, treatment, and reimplantation as a matter of course for the treatment of the B-cell tumors. At this time standard techniques for the delivery of gene therapy vectors may be used to transfect stem cells. Such transfection may result in gp41 synthesizing T-cells useful in lowering the infective levels of HIV in the patient.

II D. Non viral methods for the therapeutic delivery of nucleic acid encoding gp41

Nucleic acid encoding gp41, or a fragment thereof, under the regulation of the HIV-LTR and including the appropriate sequences required for insertion into genomic DNA of the patient, or autonomous replication, may be administered to the patient using the following gene transfer techniques: microinjection (Wolff et al., Science 247:1465 (1990)); calcium phosphate transfer (Graham and Van der Eb, Virology 52:456 (1973); Wigler et al., Cell 14:725 (1978); Felgner et al., Proc. Natl. Acad. Sci. USA 84:7413 (1987)); lipofection (Felgner et al., Proc. Natl. Acad. Sci. USA 84:7413 (1987); Ono et al., Neuroscience Lett 117:259 (1990); Brigham et al., Am. J. Med. Sci. 298:278 (1989); Staubinger and Papahadjopoulos, Meth. Enz. 101:512 (1983)); asialorosonucoid-polylysine conjugation (Wu and Wu, J. Biol. Chem. 263:14621 (1988); Wu et al., J. Biol. Chem. 264:16985 (1989)); and electroporation (Neuman et al., EMBO J. 7:841 (1980)). These references are hereby incorporated by reference.

III. Experimental Methods

1. DNA Constructs.

The 2.75 kbEcoRI-BamHI fragment (for generating TM709) and the 0.4 Kb BamHI-XhoI fragment (for generating TM752, TM775, TM795, TM812, and TM844) from HXB2R3 (Yu et al., J. Virol. 66:4966–4971 (1992)) were subcloned into pGEM7Zf(+) (Promega, Madison, Wis.). Single-stranded uracil-containing DNA was prepared and used for site-directed mutagenesis according to the protocol of the manufacturer (Bio-Rad, Richmond, Calif.). The sequences of primers used for mutagenesis were as follows: TM709, 5'-GAA TAG AGT TAG CTA GCG ATA TTC ACC AT-3' SEQ ID NO:1; TM752, 5'GTC CCA GAT AAG TGC CTA GGA TCC-3' SEQ ID NO:2; TM775, 5'-GTT ACA ATC TAG AGT AAG TC-3' SEQ ID NO:3; TM795, 5'-TAG GAG ATT CCA CTA AAA TTT GAG GGC TTC-3' SEQ ID NO:4; TM812, 5'-GTG GCA TTG AGC TAG CTA ACA GCA C-3' SEQ ID NO:5; TM844, 5'-GCC CTG TCT TAT TCC TTA AGG TAT GTG GCG AA-3' SEQ ID NO:6. Mutants were screened by restriction enzyme digestion and DNA sequencing. The 2.7 kbSalI-BamHI fragments and the 0.4 kb BamHi-XhoI fragments that contained the gp41 mutations were cloned back into the vectors of HXB2R3.

2. Cells and Sera.

COS-7 cells were maintained in Dulbecco's modified Eagle's medium containing L-glutamine and D-glucose plus 10% fetal calf serum. SupT1 and H9 cells were maintained in RPMI 1640 medium plus 10% fetal calf serum. MT2 cells were maintained in RPMI 1640 medium plus 15% fetal calf serum. PBMC were isolated by density-gradient centrifugation on LSM (Organon Teknika Corp., Durham, N.C.) and maintained in RPMI 1640 plus 20% fetal calf serum and 20 units/ml of interleukin-2 (Becton Dickinson Labware, Bedford, Mass). PBMC were treated with 5 μg/ml phytohemagglutinin PHA-P (Sigma, St. Louis, Mo.) for two days before they were used for the infection assay. The HIV positive sera and the sheep anti-gp120 serum have been previously described (Yu et al., J. Virol. 66:4966–4971 (1992)). For the immunoblot using sucrose gradient purified virions, another pooled HIV positive sera was used. Mouse monoclonal anti-gp120 antibody was obtained from Du Pont (Wilmington, Del.).

3. Transfection, Infection, and Reverse Transcriptuse (RT) Assay

Transfection and RT assay were performed as previously described (Yu et al., J. Virol. 66:4966–4971 (1992)). Briefly, subconfluent COS-7 cells ($5\times10^6$) were trypsinized and transfected with 2 μg wild type or mutant plasmid DNA by the DEAE-dextran method as previously described (Yu et al., J. Virol. 66:4966–4971 (1992)). Culture supernatants from transfected or infected cells were used to concentrate virus pellets by the polyethylene glycol method and subjected to reverse transcriptase (RT) assay as previously described (Yu et al., J. Virol. 66:4966–4971 (1992)).

4. Radioimmunoprecipitation analysis of viral proteins

At 60 h posttransfection, COS-7 cells were incubated for 12 h in cysteine-free RPMI 1640 medium containing 10% fetal calf serum and [$^{35}$S] cysteine (0.1 mCi/ml; Du Pont, Mass.). Cells were then lysed with lysis buffer (0.15M NaCl, 0.05M Tris-HCl, pH 7.2, 1% Triton X-100, 1% sodium deoxycholate, 0.1% SDS) and centrifuged at 40,000 rpm (Beckman Ti70) rotor) for 1 h to remove cell debris. Culture supernatants were precleaned at 1,000×g for 30 min and centrifuged at 40,000 rpm (Beckman Ti70 rotor) for 1 h to remove virus pellets. Cell lysates and culture supernatants were reacted with HIV positive sera that had been preabsorbed with protein A-sepharose CL-4B (Sigma, St. Louis, Mo.) for 12 h at 4° C. Samples were then washed three times with lysis buffer (without sodium deoxycholate) and once with washing buffer (0.15M NaCl, 0.05M Tris-HCl, pH 7.2). Sixty microliters of sample buffer (0.08M Tris-HCl, pH 6.8, 0.1M DTT, 2% SDS, 10% Glycerol, 0.2% bromophenol blue) were added to each sample tube. Samples were boiled for 2 min before loading and separated by 12% sodium dodecyl sulfate-polyacrylamide gel electrophoresis.

5. Purification of virions and analysis of viral proteins by immunoblot

At 72 h posttransfection, culture media from transfected COS-7 cells were centrifuged at 1000×g for 30 min. Supernatants were filtered through 0.2 µm filtration units (Nalge Company, Rochester, N.Y.) and centrifuged through 3 ml 20% sucrose cushion at 20,000 rpm (Beckman SW28 rotor) for 2 h. Virus-free supernatants were discarded and residual liquid was removed from the centrifuge tubes with dry swabs. Virus pellets were dissolved in sample buffer and separated by 12% sodium dodecyl sulfate-polyacrylamide gel electrophoresis. For further purification of the virions by sucrose gradient, virus pellets were dissolved in TNE buffer (0.01M Tris-HCl, pH 7.2, 0.1M NaCl, 0.001M EDTA) and overlaid on the top of the sucrose gradients. Sucrose gradients were prepared by a stepwise overlay of 2 ml of sucrose in TNE buffer that decreased from 60% to 20% by 2.5% increments. Samples were centrifuged at 20,000 rpm (Beckman SW28 rotor) for 20 h and 18 fractions were collected dropwise from the bottom of the centrifuge tubes. The fractions with the highest RT activity were used to isolate the virions and analyzed by immunoblot as described above.

6. Indirect Immunofluorescence Assay

Cells were washed twice with phosphate-buffered saline 60 hours posttransfection and incubated with 1:10 diluted mouse monoclonal antibody against gp120 (Du Pont, Wilmington, Del.) for 60 minutes at room temperature. Cells were then washed three times with phosphate-buffered saline and incubated with a 1:25 dilution of fluorescent isothiocyanate conjugated goat anti-mouse antibody (Becton Dickinson, San Jose, Calif.) for 45 min at room temperature. Cells were washed three times with phosphate-buffered saline and fixed with 1% paraformaldehyde before examination under a fluorescent microscope.

7. Dominant Negative Mutant Assay

To determine the presence or absence of a dominant negative phenotype conferred by a given gp41 mutant wild type or wild type-plus-mutant DNA's are transfected into SupT1 cells. Virus replication is monitored by the RT activity in the supernatant of transfected cells.

SupT1 cells (10$^7$) are washed once with phosphate-buffered saline and resuspended in 3 ml of TD buffer containing 600 µg of DEAE-dextran and 6 µg of DNA. The DNAs used for each SupT1 transfection are: mock, 6 µg of pUC18; wild type 1 µg of HXB2R3 plus µg of pUC18; wild type+mutant 1 µg of HXB2R3 plus approximately 5 µg of mutant in a suitable vector as indicated above.

Transfections are carried out at room temperature for 20 min. Virus infectivity is tested with SupT1 cells by using cell-free supernatants of transfected COS-7 cells. Samples used in the reverse transcriptase (RT) assay (provided above) are prepared from polyethylene glycol-precipitated viral pellets from the supernatant of transfected or infected cells. This assay is performed as previously described (Yu, et al., J. Virol 64:5688–5693, 1990).

IV. Mode of Therapeutic gp41 Action

The results presented herein indicate that the cytoplasmic domain of gp41 plays a critical role in HIV infectivity. Truncation of 43 (TM812), 61 (TM795), 81 (TM775), 104 (TM752), and 147 (TM709) amino acids from the cytoplasmic domain of gp41 generated noninfectious virions (FIG. 3). Analysis of these mutant virions indicated that the incorporation of viral Env proteins was significantly impaired, although other viral structural proteins were present at normal ratios when compared to the wild type virions (FIG. 4). Truncation of the last 12 amino acids from gp41 (TM844) did not significantly decrease virus assembly and release or the incorporation of viral Env proteins (FIG. 4). However, the infectivity of mutant TM844 virus was dramatically decreased compared to the wild type virus (FIG. 3). This observation suggests that the cytoplasmic domain of gp41 may also function in viral replication steps other than assembly. Since the defect of TM844 virus was more severe in H9 cells and fresh PBMC than in SupT1 and MT2 cells (FIG. 3), it appears that cellular factors could also influence the function of the gp41 cytoplasmic domain in viral replication. It has been suggested that the cytoplasmic domain of gp41 is cleaved by Vif, a potential cysteine protease (Guy et al., J. Virol. 65:1325–1331 (1987)). The putative cleavage site is very close to the stop codon introduced in the mutant TM844 (Guy et al., J. Virol. 65:1325–1331, (1987)). The observation that the wild type gp41 migrated slower than the TM844 gp41 (FIG. 3) suggests that, at least at the virion purification stage in our study, the cleavage of the cytoplasmic domain of gp41 had not occurred.

Truncation of 147 amino acids from the C-terminus of gp41 dramatically decreased the steady state level of viral Env proteins in COS-7 cells (FIG. 5). Mutant Env protein synthesis was not significantly affected as shown by pulse-chase experiments. Thus, the stability of TM709 Env proteins was apparently reduced compared to the wild type Env proteins. It was reported recently that mutations in the cytoplasmic domain of gp41 could decrease the stability of mutant Env proteins (Gabuzda et al., J. Virol. 66:3306–3315 (1992)). The TM709 gp120 migrated slightly slower than the wild type gp120 (FIG. 5), suggesting the polypeptide post-translation modifications of this gp120 in this mutant might be different from that of the wild type gp120. The decreased stability of the mutant Env proteins and the aberrant modification of mutant gp120 may indicate that the cytoplasmic domain of gp41 is important for mediating Env protein intracellular transport.

V. Examples

The following examples are provided to illustrate the invention not to limit it.

Example 1

Construction of gp41 mutants

The wild type provirus clone, HXB2R3, has been described before (Yu et al., J. Virol. 66:4966–4971 (1992)). In frame stop codons were generated at different positions in the gp41 coding region (FIG. 1, SEQ ID No. 1 and FIG. 2). The stop codon in TM709 is two amino acids downstream from the putative transmembrane region. Two positively charged arginine residues at positions 707 and 709, which are presumably important for the stop transfer signal, were preserved. TM752 and TM775 retained the first 45 and 68 amino acids of the gp41 cytoplasmic domain, respectively. Both of the predicted amphipathic 2-helices (Venable et al., AIDS Res. Hum. Retroviruses 5:7–22 (1989)) were deleted from the cytoplasmic domain of TM752 and TM775 TM proteins. Mutations in TM795 and TM812 preserved the first 88 and 106 amino acids of the gp41 cytoplasmic domain and deleted the predicted distal amphipathic α-helix (Venable et al., AIDS Res. Hum. Retroviruses 5:7–22 (1989)). The stop codon in TM844 is just upstream from the putative Vif cleavage site (Guy et al., J. Virol. 65:1325–1331 (1991)) and truncates the last 12 amino acids of gp41. The amino acids of the overlapping rev open reading frame were not affected by the nucleotide substitutions in any of the mutants.

Example 2

Infectivity of gp41 mutant viruses

Viruses were generated from COS-7 cells after transfection with wild type and mutant plasmid DNA (data not shown), suggesting that mutations in the cytoplasmic domain of gp41 did not block virus assembly and release. The infectivity of mutant viruses was compared with the wild type virus in several T-lymphoid cell lines and PBMC. Cell-free wild type and mutant viruses were prepared and analyzed for infectivity as previously described (Yu et al., J. Virol. 66:4966–4971 (1992)). Except for mutant TM844, none of the mutants established a productive infection in SupT1, MT2, and H9 cells, or fresh PBMC (FIG. 3). Although virus production was detected in TM844-infected MT-2 and SupT1 cells, the kinetics of TM844 replication in these cells was dramatically slower than that of the wild type virus (FIG. 3). The TM844 virus was at least two logs of magnitude less infectious than the wild type virus in SupT1 cells (data not shown). TM844 virus replication was even more dramatically impaired in H9 cells and PBMC, so that mutant virus production never reached the level of the wild type virus production during the thirty day follow-up period (FIG. 3).

Example 3

Analysis of virion proteins by immunoblot

Figure 4A:
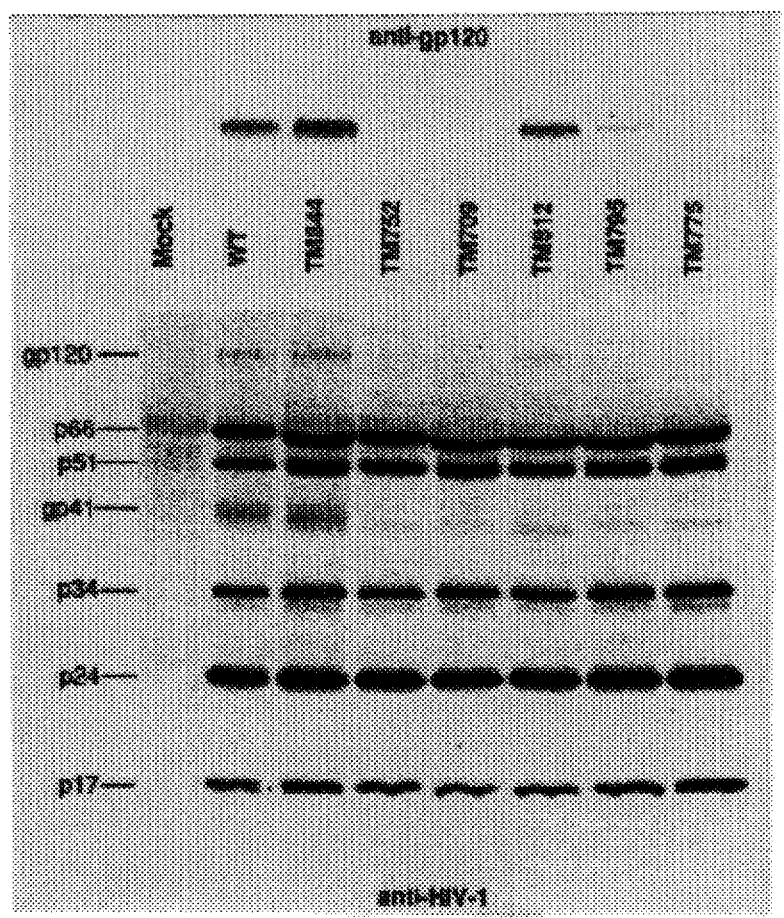

To study the defect of the mutant viruses, virions harvested from culture supernatants of wild type and mutant-transfected COS-7 cells were analyzed by immunoblot. As was the case with the wild type virions, the gag gene-encoded proteins, p24 and p17, and the pol gene-encoded proteins, p66, p51, and p34, were readily detected in all of the mutant virions using a pooled HIV positive human sera (FIG. 4a). However, in sharp contrast to the wild type virions, the level of env gene-encoded protein (gp120) detected was dramatically decreased in mutant virions TM709, TM752. TM775, or TM795 as detected by a sheep anti-gp120 serum (FIG. 4a upper panel) or the pooled HIV positive sera (FIG. 4a lower panel). Mutant gp41 was not detected in these mutant virions by HIV positive sera (FIG. 4a lower panel). For mutant TM812, no gp41 and a lesser amount of gp120 as compared to wild type virions were detected by the HIV positive sera (FIG. 3a lower panel). Comparable amounts of gp120 and gp41 were detected in wild type and mutant TM844 virions (FIG. 3a). The TM844 gp41 migrated slightly faster than the wild type gp41 (FIG. 3a).

Figure 4B:
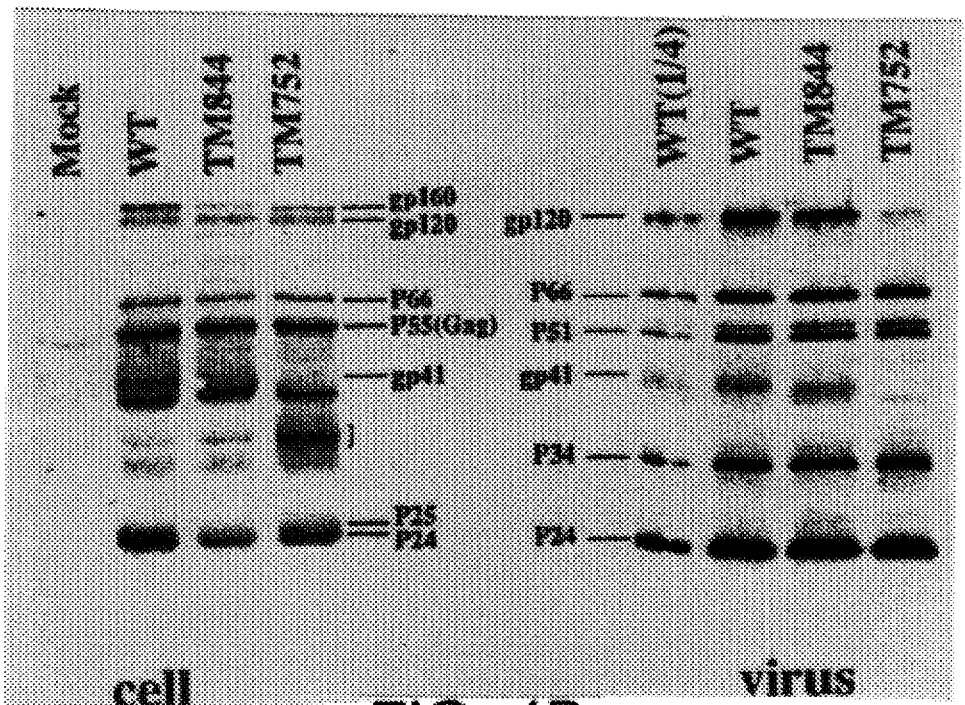

Wild type, TM844, and TM752 virions were also purified by sucrose gradients and analyzed by immunoblot using another pooled HIV positive sera. This pooled HIV positive sera reacted to gp120 better than the one used above under the stated assay conditions. The amount of gp120 and gp41 detected in mutant TM844 virions remained comparable to that of the wild type virions after purification by sucrose gradient (FIG. 4b). In contrast, the amount of gp120 detected in mutant TM752 virions was significantly less than that seen in the wild type virions (FIG. 4b). The amount of gp120 detected in TM752 virions was estimated to be less than 20% of that detected in the wild type virions when compared to a fourfold dilution of the wild type virion sample. (FIG. 4b). gp41 was not detected in the mutant TM752 virions (FIG. 4b). When cell lysates were analyzed with the same HIV positive sera, comparable amounts of gp120, and wild type and truncated gp41 were detected in wild type and TM752-transfected COS-7 cells (FIG. 4b). This suggests that the decreased detection of Env proteins in mutant TM752 virions was less likely due to a decreased immunoreactivity of the HIV positive sera.

Example 4

Figure 5A:
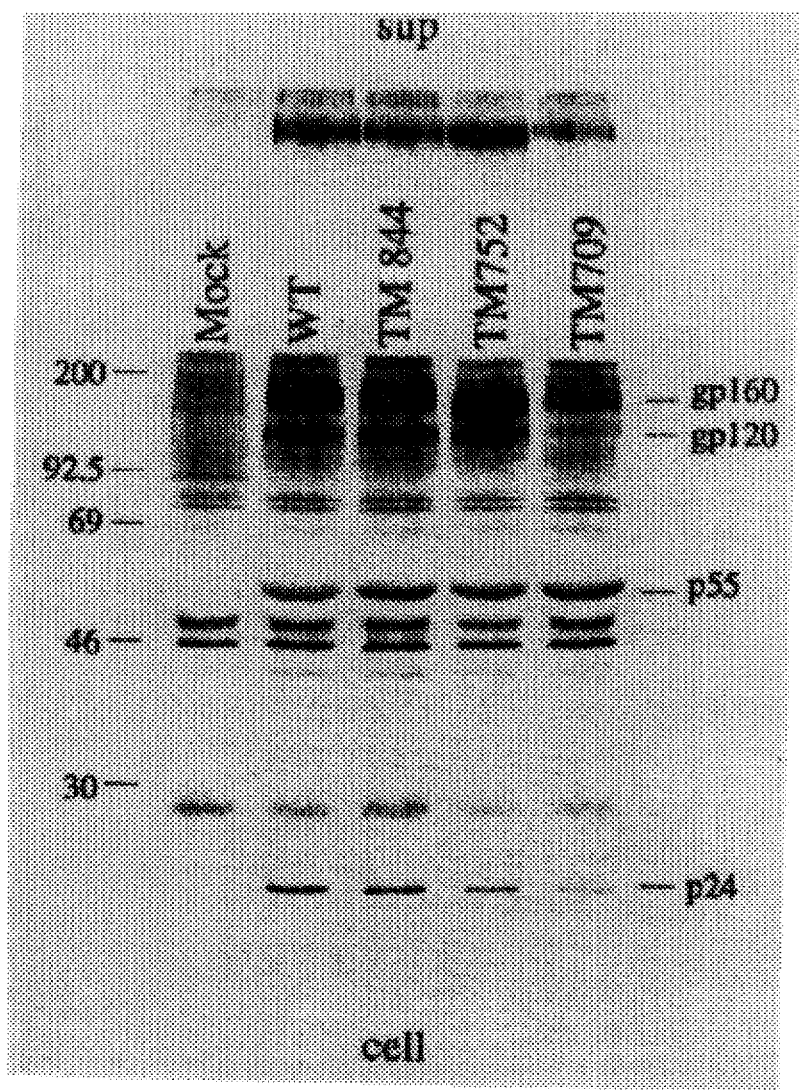

Analysis of viral Env protein synthesis, processing, transport, and surface expression To address the question of whether the decreased incorporation of Env proteins in mutant TM709 and TM752 virions was due to decreased expression of mutant Env proteins in transfected cells, the expression of viral proteins in wild type-, and in mutants TM709, TM752, and TM844-transfected COS-7 cells was analyzed by radioimmunoprecipitation. After transfection in the COS-7 cells, gp160 and gp120 were detected in the wild type-transfected cells (FIG. 5a). Similar amounts of gp160 and gp120, when adjusted for similar amounts of the Gag polyprotein (p55), were also detected in TM844- and TM752-transfected cells (FIG. 5a). The migration of TM844 and TM752 gp120 was similar to the wild type gp120 (FIG. 5a), suggesting that mutations in TM844 and TM752 did not affect the expression and processing of mutant Env proteins. The transport of TM844 and TM752 Env proteins was not significantly affected since gp120 could be detected in the supernatants of TM844 and TM852-transfected cells (FIG. 5a). The amount of gp160 and gp120 detected in the TM709-transfected cells was much less than that detected in the wild type-transfected cells (FIG. 5a). In addition, TM709 gp120 migrated slightly slower than the wild type gp120 (FIG. 5a). TM709 gp120 was detected in the culture supernatant of TM709-transfected COS-7 cells (FIG. 4a). This suggests that Env protein transport to the cell surface could still occur in TM709-transfected cells.

Figure 5B:
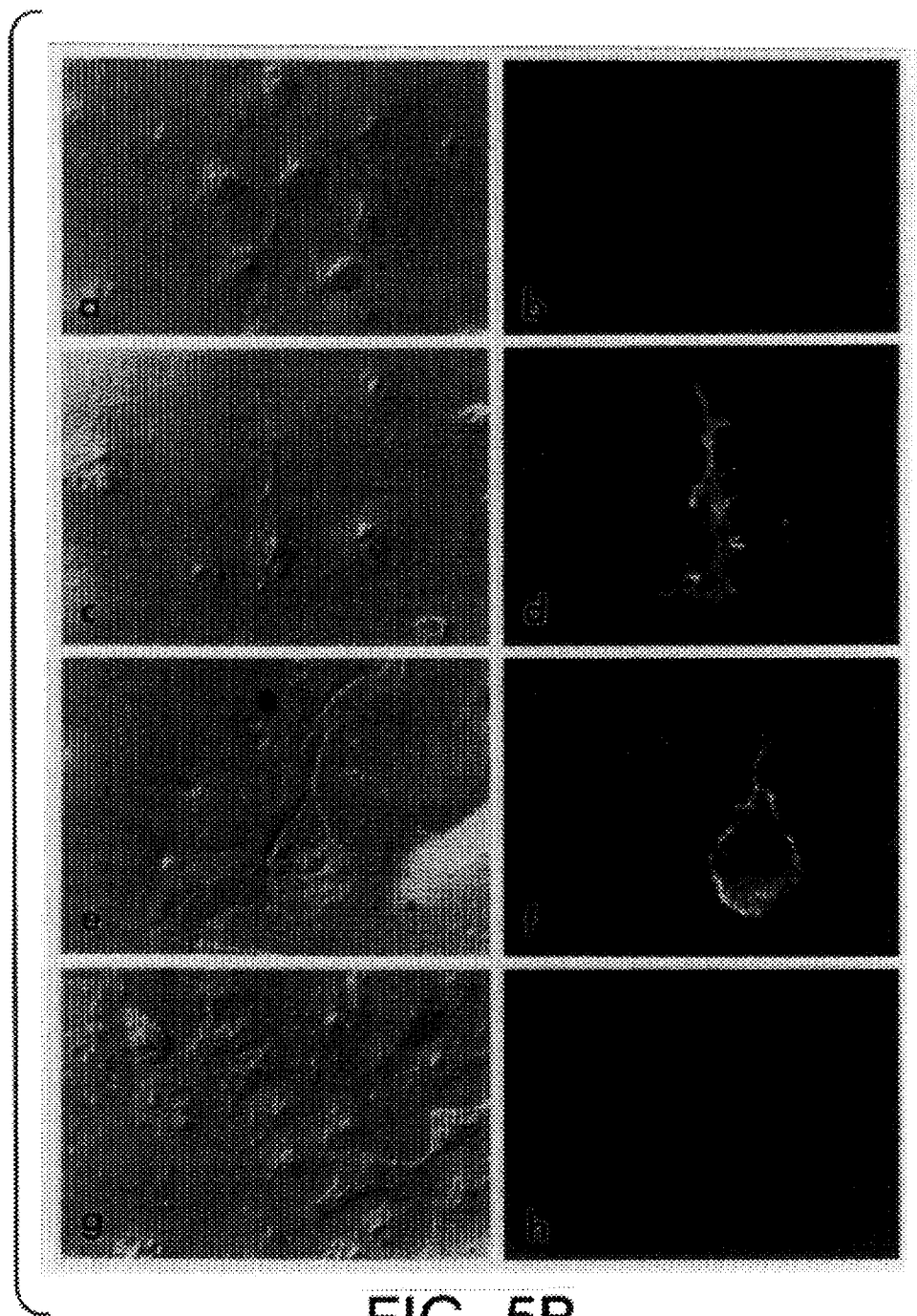

Surface expression of the gp120 in wild type, TM752- and TM709- transfected COS-7 cells were also studied by indirect immunofluorescence staining. Comparable levels of gp120 were detected on the surface of wild type- and TM752-transfected cells by mouse monoclonal anti-gp120 antibody (FIG. 4b). This indicates that the surface anchorage of gp120 was not affected by the truncation of the cytoplasmic domain in TM752. This observation is in agreement with previous reports where truncation of the last 104 amino acids from the C terminus of gp41 (same as TM752) did not affect the surface expression of the viral Env protein (Earl et al., J. Virol. 65:31–41 (1991)). In contrast to TM752, the ability of mutant TM709 to express Env proteins on the cell surface was greatly diminished as indicated by the lack of immunofluorescence staining of gp120 on the surface of the TM709-transfected COS-7 cells (FIG. 5b).

VI. Other Embodiments gp41 Polypeptides

As described above, the invention includes therapies using a protein (or nucleic acid encoding a protein), which are mutant HIV gp41 proteins described elsewhere in this application, or which are homologous to such mutants. Also included are: allelic variations; natural mutants; induced mutants; proteins encoded by DNA that hybridizes under high (e.g., washing at 2×SSC at 40° C. with a probe length of at least 40 nucleotides) stringency conditions to naturally occurring gp41 encoding nucleic acid (for other definitions of high and low stringency see Current Protocols in Molecular Biology, John Wiley & Sons, New York, 1989, 6.3.1–6.3.6, hereby incorporated by reference). The term also includes chimeric polypeptides that include gp41 together with unrelated sequences.

The invention also includes any biologically active fragment or analog of gp41. By "biologically active" is meant possessing therapeutically useful anti-HIV activity which is characteristic of the gp41 encoding by the constructs shown in FIGS. 2 and 7 and described in Section I of the specification. Therapeutically useful activity of a gp41 fragment or gp41 analog, can be determined in any one (or more) of a variety of assays, for example, those assays described in this application such as the dominant negative mutant assay. A gp41 analog possessing, most preferably greater than a five fold decrease over wild type in the dominant negative assay between the 1 and 10 day assay period, preferably a four fold decrease, or at least twofold decrease over the anti-HIV activity of an unchallenged control infection with wild type HIV in any in vivo or in vitro gp41 assay for anti-HIV activity (e.g., those described), is considered biologically active and useful in the invention.

Preferred analogs include mutant gp41 (or biologically active fragments thereof) whose sequences differ from the indicated gp41 mutant sequences only by conservative amino acid substitutions, for example, substitution of one amino acid for another of the same class (e.g., valine for glycine, arginine for lysine, etc.) or by one or more non-conservative amino acid substitutions, deletions, or insertions which do not destroy the polypeptide's relevant anti-HIV activity as measured using in vivo or in vitro (e.g., using the infectivity and dominant negative assays described above). Preferred analogs also include gp41 (or active fragments thereof) which are modified for the purpose of increasing peptide stability; such analogs may contain, for example, one or more desaturated peptide bonds or D-amino acids in the peptide sequence.

Analogs can differ from naturally occurring gp41 by amino acid sequence differences or by modifications that do not affect sequence, or by both. Analogs of the invention will generally exhibit at least 65%, more preferably 80%, even more preferably 90%, and most preferably 95% or even 99%, homology with all or part of a naturally occurring gp41 sequence. The length of comparison sequences will generally be at least about 15 amino acid residues, preferably more than 40 amino acid residues. Modifications include in vivo, or in vitro chemical derivatization of polypeptides, e.g., acetylation, glycosylation, or carboxylation. Also embraced are versions of the same primary amino acid sequence that have phosphorylated amino acid residues, e.g., phosphotyrosine, phosphoserine, or phosphothreonine. Analogs can differ from naturally occurring gp41 by alterations of their primary sequence. These include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of gp41 can be generated by methods known to those skilled in the art. The ability of a candidate fragment to exhibit a biological activity of gp41 can be assessed by methods described below. Also included are gp41 polypeptides containing amino acids that are normally removed during protein processing, including additional amino acids that are not required for the therapeutic activity of the polypeptide, or including additional amino acids that result from alternative mRNA splicing or alternative protein processing events.

The invention also includes polypeptides (or nucleic acid either encoding polypeptides) which are homologous to the gp41 protein or homologous to the gp160 gene and are useful for the treatment of individuals infected with HIV. Sequences which are considered to be homologous are those which are 70% homologous. Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

---

What is claimed is:

1. A nucleic acid encoding a mutant gp41 polypeptide containing a deletion of any one of the following regions of wild type gp41:
   amino acids 844 to 856;
   amino acids 796 to 856;
   amino acids 776 to 856;
   amino acids 753 to 856; or
   amino acids 710 to 856, said deletions being effective to either disrupt viral replication of HIV or disrupt the assembly of viral Env proteins in an HIV infected cell.

2. The nucleic acid of claim 1 in an expressible genetic construction for transforming cells.

3. The nucleic acid of claim 2 comprising said nucleic acid as part of a viral vector capable of transforming cells.

4. The nucleic acid of claim 2 wherein said nucleic acid further comprises a sequence capable of encoding a CD4-binding polypeptide.

5. The nucleic acid of claim 2 wherein said nucleic acid further comprises a sequence encoding a gp120-binding polypeptide.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 29
        ( B ) TYPE: nucleic acid
        ( C ) STRANDEDNESS: double
        ( D ) TOPOLOGY: linear ( x i ) SEQUENCE DESCRIPTION: SEQ ID NO: 1:

GAATAGAGTT AGCTAGCGAT ATTCACCAT                    29

( 2 ) INFORMATION FOR SEQ ID NO: 2:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( x i ) SEQUENCE DESCRIPTION: SEQ ID NO: 2:

GTCCCAGATA AGTGCCTAGG ATCC                          24

( 2 ) INFORMATION FOR SEQ ID NO: 3:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO: 3:

GTTACAATCT AGAGTAAG                                 18

( 2 ) INFORMATION FOR SEQ ID NO: 4:

( i ) SEQUENCE CHARACTERISTICS:
        ( A ) LENGTH: 30
        ( B ) TYPE: nucleic acid
        ( C ) STRANDEDNESS: double
        ( D ) TOPOLOGY: linear ( x i ) SEQUENCE DESCRIPTION: SEQ ID NO: 4:

TAGGAGATTC CACTAAAATT TGAGGGCTTC                    30

( 2 ) INFORMATION FOR SEQ ID NO: 5:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( x i ) SEQUENCE DESCRIPTION: SEQ ID NO: 5:

GTGGCATTCA GCTAGCTAAC AGCA                          24

( 2 ) INFORMATION FOR SEQ ID NO: 6:

( i ) SEQUENCE CHARACTERISTICS:
        ( A ) LENGTH: 32
        ( B ) TYPE: nucleic acid
        ( C ) STRANDEDNESS: double
        ( D ) TOPOLOGY: linear ( x i ) SEQUENCE DESCRIPTION: SEQ ID NO: 6:

GCCCTGTCTT ATTCCTTAAG GTATGTGGCG AA    32

( 2 ) INFORMATION FOR SEQ ID NO: 7:

( i ) SEQUENCE CHARACTERISTICS:
        ( A ) LENGTH: 1260
        ( B ) TYPE: nucleic acid
        ( C ) STRANDEDNESS: double
        ( D ) TOPOLOGY: linear ( x i ) SEQUENCE DESCRIPTION: SEQ ID NO: 7:

```
ACCTGGAGGA GGAGATATGA GGGACAATTG GAGAAGTGAA TTATATAAAT ATAAAGTAGT        60

AAAAATTGAA CCATTAGGAG TAGCACCCAC CAAGGCAAAG AGAAGAGTGG TGCAGAGAGA       120

AAAAAGA GCA GTG GGA ATA GGA GCT TTG TTC CTT GGG TTC TTG GGA GCA        169
        Ala Val Gly Ile Gly Ala Leu Phe Leu Gly Phe Leu Gly Ala
         1          5                        10

GCA GGA AGC ACT ATG GGC GCA GCG TCA ATG ACG CTG ACG GTA CAG GCC        217
Ala Gly Ser Thr Met Gly Ala Ala Ser Met Thr Leu Thr Val Gln Ala
 15              20                  25                      30

AGA CAA TTA TTG TCT GGT ATA GTG CAG CAG CAG AAC AAT TTG CTG AGG        265
Arg Gln Leu Leu Ser Gly Ile Val Gln Gln Gln Asn Asn Leu Leu Arg
             35                  40                      45

GCT ATT GAG GCG CAA CAG CAT CTG TTG CAA CTC ACA GTC TGG GGC ATC        313
Ala Ile Glu Ala Gln Gln His Leu Leu Gln Leu Thr Val Trp Gly Ile
         50                  55                      60

AAG CAG CTC CAG GCA AGA ATC CTG GCT GTG GAA AGA TAC CTA AAG GAT        361
Lys Gln Leu Gln Ala Arg Ile Leu Ala Val Glu Arg Tyr Leu Lys Asp
         65                  70                      75

CAA CAG CTC CTG GGG ATT TGG GGT TGC TCT GGA AAA CTC ATT TGC ACC        409
Gln Gln Leu Leu Gly Ile Trp Gly Cys Ser Gly Lys Leu Ile Cys Thr
         80                  85                      90

ACT GCT GTG CCT TGG AAT GCT AGT TGG AGT AAT AAA TCT CTG GAA CAG        457
Thr Ala Val Pro Trp Asn Ala Ser Trp Ser Asn Lys Ser Leu Glu Gln
 95              100                 105                     110

ATT TGG AAT CAC ACG ACC TGG ATG GAG TGG GAC AGA GAA ATT AAC AAT        505
Ile Trp Asn His Thr Thr Trp Met Glu Trp Asp Arg Glu Ile Asn Asn
             115                 120                     125

TAC ACA AGC TTA ATA CAC TCC TTA ATT GAA GAA TCG CAA AAC CAG CAA        553
Tyr Thr Ser Leu Ile His Ser Leu Ile Glu Glu Ser Gln Asn Gln Gln
             130                 135                     140

GAA AAG AAT GAA CAA GAA TTA TTG GAA TTA GAT AAA TGG GCA AGT TTG        601
Glu Lys Asn Glu Gln Glu Leu Leu Glu Leu Asp Lys Trp Ala Ser Leu
         145                 150                     155

TGG AAT TGG TTT AAC ATA ACA AAT TGG CTG TGG TAT ATA AAA TTA TTC        649
Trp Asn Trp Phe Asn Ile Thr Asn Trp Leu Trp Tyr Ile Lys Leu Phe
 160                 165                     170

ATA ATG ATA GTA GGA GGC TTG GTA GGT TTA AGA ATA GTT TTT GCT GTA        697
Ile Met Ile Val Gly Gly Leu Val Gly Leu Arg Ile Val Phe Ala Val
 175                 180                     185                 190

CTT TCT ATA GTG AAT AGA GTT AGG CAG GGA TAT TCA CCA TTA TCG TTT        745
Leu Ser Ile Val Asn Arg Val Arg Gln Gly Tyr Ser Pro Leu Ser Phe
             195                 200                     205

CAG ACC CAC CTC CCA ACC CCG AGG GGA CCC GAC AGG CCC GAA GGA ATA        793
Gln Thr His Leu Pro Thr Pro Arg Gly Pro Asp Arg Pro Glu Gly Ile
             210                 215                     220

GAA GAA GAA GGT GGA GAG AGA GAC AGA GAC AGA TCC ATT CGA TTA GTG        841
Glu Glu Glu Gly Gly Glu Arg Asp Arg Asp Arg Ser Ile Arg Leu Val
         225                 230                     235

AAC GGA TCC TTG GCA CTT ATC TGG GAC GAT CTG CGG AGC CTG TGC CTC        889
Asn Gly Ser Leu Ala Leu Ile Trp Asp Asp Leu Arg Ser Leu Cys Leu
 240                 245                     250

TTC AGC TAC CAC CGC TGG AGA GAC TTA CTC TTG ATT GTA ACG AGG ATT        937
Phe Ser Tyr His Arg Trp Arg Asp Leu Leu Leu Ile Val Thr Arg Ile
 255                 260                     265                 270

GTG GAA CTT CTG GGA CGC AGG GGG TGG GAA GCC CTC AAA TAT TGG TGG        985
Val Glu Leu Leu Gly Arg Arg Gly Trp Glu Ala Leu Lys Tyr Trp Trp
             275                 280                     285

AAT CTC CTA CAG TAT TGG AGT CAG GAA CTA AAG AAT AGT GCT GTT AGC       1033
Asn Leu Leu Gln Tyr Trp Ser Gln Glu Leu Lys Asn Ser Ala Val Ser
             290                 295                     300
```

```
TTG CTC AAT GCC ACA GCC ATA GCA GTA GCT GAG GGG ACA GAT AGG GTT         1081
Leu Leu Asn Ala Thr Ala Ile Ala Val Ala Glu Gly Thr Asp Arg Val
        305             310                 315

ATA GAA GTA GTA CAA GGA GCT TGT AGA GCT ATT CGC CAC ATA CCT AGA         1129
Ile Glu Val Val Gln Gly Ala Cys Arg Ala Ile Arg His Ile Pro Arg
    320                 325                 330

AGA ATA AGA CAG GGC TTG GAA AGG ATT TTG CTA  TAAGATGGGT                 1172
Arg Ile Arg Gln Gly Leu Glu Arg Ile Leu Leu
335             340                 345

GGCAAGTGGT CAAAAAGTAG TGTGATTGGA TGGCTTACTG TAAGGGAAAG AATGAGACGA       1232

GCTGAGCCAG CAGCAGATGG GGTGGGAG                                          1260
```